(12) United States Patent
Jaryal et al.

(10) Patent No.: US 8,618,305 B2
(45) Date of Patent: Dec. 31, 2013

(54) SORAFENIB DIMETHYL SULPHOXIDE SOLVATE

(75) Inventors: Jagdev Singh Jaryal, Kangra (IN); Swargam Sathyanarayana, Karim Nagar (IN); Rajesh Kumar Thaper, Jammu (IN); Mohan Prasad, Gurgaon (IN); Sachin Deorao Zade, Yavatmal (IN); Ajay Shankar Singh, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/575,057

(22) PCT Filed: Jan. 28, 2011

(86) PCT No.: PCT/IB2011/050396
§ 371 (c)(1),
(2), (4) Date: Apr. 3, 2013

(87) PCT Pub. No.: WO2011/092663
PCT Pub. Date: Aug. 4, 2011

(65) Prior Publication Data
US 2013/0210865 A1    Aug. 15, 2013

(30) Foreign Application Priority Data

Jan. 29, 2010 (IN) .............................. 204/DEL/2010

(51) Int. Cl.
*A61K 31/44* (2006.01)
*C07D 213/81* (2006.01)

(52) U.S. Cl.
USPC ...................... 546/268.1; 514/350

(58) Field of Classification Search
None
See application file for complete search history.

(56) References Cited

U.S. PATENT DOCUMENTS

2009/0192200 A1    7/2009    Gavenda et al. .............. 514/350

FOREIGN PATENT DOCUMENTS

| WO | WO 00/42012 | 7/2000 | ........... C07D 211/78 |
|---|---|---|---|
| WO | WO 2004/113274 | 12/2004 | ........... G01N 33/574 |
| WO | WO 2006/034796 | 4/2006 | ........... C07D 213/81 |
| WO | WO 2006/034797 | 4/2006 | ........... C07D 213/81 |
| WO | WO 2006/094626 | 9/2006 | ............... A61K 9/20 |
| WO | WO 2008/082487 | 7/2008 | ........... C07D 213/81 |
| WO | WO 2009/034308 | 3/2009 | ........... C07C 233/65 |
| WO | WO 2009/054004 | 4/2009 | ........... C07D 213/81 |
| WO | WO 2009/092070 | 7/2009 | ........... C07D 213/81 |
| WO | WO 2009/106825 | 9/2009 | ........... C07D 213/89 |
| WO | WO 2009/111061 | 9/2009 | ........... C07D 213/81 |

OTHER PUBLICATIONS

Pope and Oliver, "Dimethyl Sulfoxide (DMSO)", *Canadian Journal of Comparative Medicine and Veterinary Science*, 30(1):3-8 (1966).
Blanchet et al., "Validation of an HPLC-UV method for sorafenib determination in human plasma and application to cancer patients in routine clinical practice", *Journal of Pharmaceutical and Biomedical Analysis*, 49(4):1109-1114 (2009).
Afify et al.,"Validation of a liquid chromatography assay for the quantification of the Raf kinase inhibitor BAY 43-9006 in small volumes of mouse serum", *Journal of Chromatography B*, 809(1):99-103 (2004).

*Primary Examiner* — Janet Andres
*Assistant Examiner* — Heidi Reese

(57) ABSTRACT

The present invention provides dimethyl sulphoxide solvate of 4-(4-{3-[4-chloro-3 -(trifluoromethyl)phenyl]ureido}phenoxy)-$N^2$-methylpyridine-2-carboxamide, process for its preparation, pharmaceutical composition comprising it and its use for the treatment of cancer. The present invention also provides a novel HPLC method for the identification, quantification and isolation of related substances of sorafenib.

12 Claims, 10 Drawing Sheets

PEAK RESULTS

| | Name | Retention Time (min) | Area (μV*sec) | % Area | RT ratio | Int Type |
|---|---|---|---|---|---|---|
| 1 | Peak 1 | 36.01 | 10949 | 0.19 | 0.97 | BB |
| 2 | Peak 2 | 37.00 | 5905786 | 99.81 | | BB |

SORAFENIB DIMETHYL SULPHOXIDE SOLVATE

FIELD OF THE INVENTION

The present invention provides a dimethyl sulphoxide solvate of 4-(4-{3-[-4-chloro-3-(trifluoromethyl)phenyl]ureido}phenoxy)-$N^2$-methylpyridine-2-carboxamide, a process for its preparation, a pharmaceutical composition comprising it and its use for the treatment of cancer. The present invention also provides a novel HPLC method for the identification, quantification and isolation of related substances of sorafenib.

BACKGROUND OF THE INVENTION 4-(4-{3-[4-Chloro-3-(trifluoromethyl)phenyl]ureido}phenoxy)-$N^2$-methylpyridine-2-carboxamide, having the structure as represented by Formula I

FORMULA I is marketed in the United States as its tosylate salt (sorafenib tosylate) of Formula II

FORMULA II under the brand name Nexavar® for the treatment of patients with unresectable hepatocellular carcinoma and advanced renal cell carcinoma.

WO 2006/034797 discloses ethanol and methanol solvates of sorafenib tosylate.

U.S. Patent Publication 2009/192200 discloses dimethyl sulphoxide and N-methylpyrrolidone solvates of sorafenib tosylate.

SUMMARY OF THE INVENTION

The present invention provides safe and industrially advantageous dimethyl sulphoxide solvate of sorafenib, process for its preparation, pharmaceutical composition comprising it and its use for the treatment of cancer.

Sorafenib dimethyl sulphoxide solvate of the present invention is a free-flowing non-hygroscopic solid and is stable towards heating up to a temperature of 110° C. under reduced pressure.

The present invention also provides processes for the preparation of sorafenib free base and sorafenib acid addition salts and a novel and efficient HPLC method capable of separating all related substances of sorafenib.

A first aspect of the present invention provides sorafenib dimethyl sulphoxide solvate of Formula III

FORMULA III characterized by X-ray diffraction peaks at d-spacing 5.20, 4.21, 4.16, 3.83 and 3.66 Å.

A second aspect of the present invention provides a process for the preparation of sorafenib dimethyl sulphoxide solvate of Formula III.

FORMULA III comprising contacting sorafenib free base of Formula I

FORMULA I with dimethyl sulphoxide.

A third aspect of the present invention provides process for the preparation of sorafenib free base of Formula I

FORMULA I comprising contacting sorafenib dimethyl sulphoxide solvate of Formula III

FORMULA III with a solvent.

A fourth aspect of the present invention provides a process for the preparation of sorafenib free base of Formula I

FORMULA I comprising heating sorafenib dimethyl sulphoxide solvate of Formula III

FORMULA III above 110° C.

A fifth aspect of the present invention provides a process for the preparation of sorafenib acid addition salts of Formula IV

FORMULA IV comprising contacting sorafenib dimethyl sulphoxide solvate of Formula III with an acid of Formula HX and isolating sorafenib acid addition salt of Formula IV.

A sixth aspect of the present invention provides a pharmaceutical composition comprising sorafenib dimethyl sulphoxide solvate of Formula III and one or more pharmaceutically acceptable carriers, diluents or excipients.

A seventh aspect of the present invention provides use of sorafenib dimethyl sulphoxide solvate of Formula III for the treatment of cancer.

An eighth aspect of the present invention provides an HPLC method for the identification, quantification and isolation of related substances of sorafenib, pharmaceutically acceptable salts, polymorphs, pseudomorphs and solvates thereof comprising the use of a buffer and a single organic solvent as mobile phase.

A ninth aspect of the present invention provides sorafenib or pharmaceutically acceptable salts, polymorphs, pseudomorphs and solvates thereof substantially free of related substances determined by area percentage of HPLC.

Other objects, features, advantages and aspects of the present invention will become apparent to those skilled in the art from the description provided herein.

DETAILED DESCRIPTION OF THE INVENTION

Various embodiments and variants of the present invention are described hereinafter.

The term "related substance", as used herein, refers to any known or unknown compound (impurity) present in the sample. A related substance may be introduced in the sample as a process impurity or it may be formed due to degradation. Some related substances may even be of unknown origin.

The term "sample", as used herein, refers to the material analyzed by any analytical technique, including chromatography. It may consist of a single component or a mixture of components. In the present invention, a sample may consist of sorafenib or pharmaceutically acceptable salts, polymorphs, pseudomorphs, and solvates thereof.

The term "mobile phase", as used herein, refers to the solvent that moves the sample through the column. The mobile phase used for the identification, quantification or isolation of related substances of sorafenib may comprise a buffer and a single organic solvent.

The buffer may be selected from acidic phosphate, citrate, formate or acetate buffers, such as orthophosphoric acid or trifluoroacetic acid. Preferably, an acidic buffer, such as orthophosphoric acid may be used.

The organic solvent to be used may be selected from the group consisting of alcohols, alkyl acetates and alkyl nitriles. Examples of alcohols include methanol, ethanol, n-propanol, isopropanol, n-butanol, sec-butanol, isobutanol, n-pentanol, ethylene glycol and propylene glycol. Examples of alkyl acetates include methyl acetate, ethyl acetate, propyl acetate and butyl acetate. Examples of nitriles include acetonitrile and propionitrile. Preferably, alcohols, such as methanol, ethanol, n-propanol, isopropanol, n-butanol, sec-butanol, isobutanol, n-pentanol, ethylene glycol or propylene glycol are used.

The term "retention time", as used herein, refers to the characteristic time taken by a particular sample to pass through the system (from the column inlet to the detector) under a set of conditions.

The term "relative retention time", as used herein, refers to the ratio between the retention time of a related substance and that of sorafenib.

The term "substantially free of related substances determined by area percentage of HPLC", as used herein, refers to sorafenib, pharmaceutically acceptable salts, polymorphs, pseudomorphs and solvates thereof having no detectable amount of related substances 4-(2-(N-methylcarbamonyl)-4-(pyridyloxy)aniline, 4-chloro-N-methyl-2-pyridinecarboxamide and 4-chloro-3-(trifluoromethyl)phenyl isocyanate as determined by area percentage of HPLC at relative retention time of 0.50, 0.64 and 0.88 minutes, respectively.

The term "contacting" may include dissolving, slurrying, stirring or a combination thereof.

Sorafenib dimethyl sulphoxide solvate of Formula III may be characterized by X-ray diffraction peaks at about 17.04 (d-spacing at 5.20 Å), 21.05 (4.21 Å), 21.34 (4.16 Å), 23.19 (3.83 Å) and 24.28 (3.66 Å) ±0.2 degrees 2θ. It may be further characterized by X-ray diffraction peaks at about 16.52 (5.36 Å), 19.85 (4.47 Å), 19.98 (4.44 Å), 27.30 (3.26 Å) and 28.34 (3.14 Å) ±0.2 degrees 2θ. It may also be characterized by a DSC thermogram having endotherms at about 123.69° C. and about 202.54° C. Sorafenib dimethyl sulphoxide solvate of Formula III may also be characterized by its XRD pattern, DSC thermogram, TGA curve and IR spectrum as depicted in FIGS. 1, 2, 3 and 4, respectively. Table-1 summarizes the d-spacing in Å and the corresponding 2θ values of sorafenib dimethyl sulphoxide solvate of Formula III. Sorafenib dimethyl sulphoxide of Formula III may have a moisture content of about 0.1% by Karl-Fischer method.

TABLE 1

X-ray Diffraction Peaks of Sorafenib Dimethyl Sulphoxide Solvate

| Position (°2θ) | d-spacing (Å) | Relative Intensity (%) |
| --- | --- | --- |
| 6.80 | 13.01 | 1.89 |
| 8.48 | 10.43 | 7.97 |
| 9.34 | 9.47 | 1.58 |
| 10.21 | 8.66 | 2.10 |
| 11.42 | 7.75 | 9.78 |
| 12.22 | 7.24 | 8.49 |
| 12.70 | 6.97 | 12.27 |
| 15.64 | 6.49 | 11.70 |
| 13.87 | 6.38 | 19.62 |
| 14.06 | 6.30 | 23.66 |
| 14.94 | 5.93 | 10.52 |
| 15.46 | 5.73 | 18.35 |
| 15.62 | 5.67 | 17.16 |
| 16.52 | 5.36 | 29.12 |
| 17.04 | 5.20 | 49.13 |
| 17.82 | 4.98 | 24.11 |
| 18.74 | 4.73 | 21.67 |
| 19.09 | 4.65 | 12.73 |
| 19.36 | 4.59 | 11.21 |
| 19.64 | 4.52 | 14.14 |
| 19.85 | 4.47 | 36.50 |
| 19.98 | 4.44 | 35.03 |
| 20.52 | 4.33 | 25.78 |
| 20.79 | 4.27 | 20.54 |
| 21.05 | 4.21 | 65.56 |
| 21.34 | 4.16 | 68.00 |
| 23.19 | 3.83 | 52.91 |
| 24.17 | 3.68 | 74.03 |
| 24.28 | 3.66 | 100.00 |
| 24.78 | 3.59 | 25.64 |
| 25.18 | 3.54 | 15.20 |
| 25.60 | 3.48 | 15.16 |
| 25.89 | 3.44 | 17.19 |
| 26.47 | 3.37 | 16.35 |
| 27.30 | 3.26 | 28.72 |
| 27.96 | 3.19 | 8.68 |
| 28.34 | 3.14 | 26.78 |
| 28.76 | 3.10 | 11.90 |
| 29.26 | 3.05 | 12.59 |
| 29.52 | 3.03 | 7.51 |
| 29.86 | 2.99 | 5.68 |
| 31.00 | 2.88 | 5.36 |
| 31.49 | 2.84 | 9.73 |
| 32.30 | 2.77 | 5.55 |
| 33.06 | 2.71 | 3.59 |
| 33.81 | 2.65 | 7.96 |
| 34.64 | 2.59 | 4.76 |
| 36.20 | 2.48 | 5.17 |
| 38.06 | 2.36 | 7.31 |
| 38.76 | 2.32 | 6.13 |

Sorafenib free base to be used for the preparation of sorafenib dimethyl sulphoxide solvate of Formula III may be obtained by any of the methods known in the literature such as those described in PCT applications WO 00/42012, WO 2006/034796, WO 2009/034308 and WO 2009/054004, which are incorporated herein by reference.

In general, sorafenib free base to be used for the preparation of sorafenib dimethyl sulphoxide solvate may be prepared by the reaction of 4-(2-(N-methylcarbamoyl)-4-pyridyloxy)aniline with 4-chloro-3-(trifluoromethyl)phenyl isocyanate. The starting sorafenib freebase may be obtained as a solution directly from a reaction in which it is formed and used as such without isolation.

Sorafenib free base of Formula I may be contacted with dimethyl sulphoxide at a temperature of about 15° C. to the reflux temperature of dimethyl sulphoxide. In experiments involving contacting sorafenib free base with dimethyl sulphoxide at room temperature, the reaction mixture may be stirred for about 2 hours to about 8 hours. In experiments involving contacting sorafenib free base with dimethyl sulphoxide at a temperature above room temperature, the reaction mixture may be stirred for about 5 minutes to about 30 minutes, slowly cooled to a temperature of 20° C. to about 25° C. in about 5 minutes to about 30 minutes followed by further stirring for about 1 hour to about 10 hours.

Isolation may be accomplished by concentration, precipitation, cooling, filtration or centrifugation, preferably by precipitation and filtration. The filtered material may be optionally washed with water and dried at a temperature of about 40° C. to about 65° C., for about 30 minutes to about 24 hours. Any suitable method of drying may be employed such as drying under reduced pressure, vacuum tray drying, air drying or a combination thereof.

In one embodiment, sorafenib dimethyl sulphoxide solvate of Formula III may be prepared by adding dimethyl sulphoxide to sorafenib free base of Formula I, stirring the reaction mixture at a temperature of about 35° C. to about 80° C., for about 5 minutes to about 30 minutes, cooling the solution to a temperature of about 20° C. to about 35° C. in about 5 minutes to about 30 minutes, stirring the reaction mixture for about 1 hour to about 2 hours and isolating sorafenib dimethyl sulphoxide solvate. In a preferred embodiment, sorafenib dimethyl sulphoxide solvate of Formula III may be prepared by adding dimethyl sulphoxide to sorafenib free base of Formula I, stirring the reaction mixture at about 45° C. for about 10 minutes, cooling the solution to a temperature of about 25° C. in about 15 minutes, stirring the reaction mixture for about 2 hours and isolating sorafenib dimethyl sulphoxide solvate. In another preferred embodiment, sorafenib dimethyl sulphoxide solvate of Formula III may be prepared by adding dimethyl sulphoxide to sorafenib free base of Formula I, stirring the reaction mixture at about 60° C. for about 20 minutes, cooling the reaction mixture to about 25° C. in about 15 minutes, stirring for about 8 hours and isolating sorafenib dimethyl sulphoxide solvate.

In another embodiment, sorafenib dimethyl sulphoxide solvate of Formula III may be prepared by adding dimethyl sulphoxide to sorafenib free base of Formula I at room temperature, stirring the reaction mixture for about 1 hour to about 8 hours and isolating sorafenib dimethyl sulphoxide solvate.

Sorafenib dimethyl sulphoxide solvate of Formula III has HPLC purity greater than 99%. In one embodiment, the HPLC purity is greater than 99.4%. In another embodiment, the HPLC purity is greater than 99.7%.

The term "thermally stable sorafenib dimethyl sulphoxide solvate of Formula III", as used herein, refers to sorafenib dimethyl sulphoxide solvate of Formula III stable towards heating, to a temperature up to 110° C., in a vacuum oven. Preferably, sorafenib dimethyl sulphoxide solvate of Formula III of the present invention is stable towards heating in the temperature range of about 45° C. up to 110° C. for about 3 hours to about 4 hours in a vacuum oven. Desolvation of sorafenib dimethyl sulphoxide solvate to sorafenib free base may occur on heating at a temperature of about 120° C. to about 135° C.

Sorafenib dimethyl sulphoxide solvate of the present invention is a free-flowing non-hygroscopic powder.

Sorafenib free base of Formula I may be prepared from sorafenib dimethyl sulphoxide solvate of Formula III by contacting sorafenib dimethyl sulphoxide solvate with a solvent at a temperature of about −5° C. to the reflux temperature of the solvent. The solvent is selected from the group consisting of water, chlorinated hydrocarbons, alcohols, ketones, alkyl acetates, ethers and mixtures thereof. Examples of chlorinated hydrocarbons include dichloromethane and chloroform. Examples of alcohols include methanol, ethanol, isopropanol and butanol. Examples of ketones include acetone, dimethyl ketone, ethyl methyl ketone and methyl iso-butyl ketone. Examples of alkyl acetates include methyl acetate, ethyl acetate, propyl acetate and butyl acetate. Examples of ethers include diethyl ether, ethyl methyl ether, tetrahydrofuran and 1,4-dioxane.

Precipitation of sorafenib free base from the reaction mixture of sorafenib dimethyl sulphoxide solvate in a solvent may be spontaneous or it may occur after stirring the reaction mixture for about 1 hour to about 8 hours.

In a particular embodiment, sorafenib free base of Formula I may be prepared by contacting sorafenib dimethyl sulphoxide solvate of Formula III with water at room temperature. The reaction mixture may be optionally heated to a temperature of about 40° C. or above. The reaction mixture may be stirred for about 2 hours to about 24 hours. In a preferred embodiment, sorafenib free base of Formula I may be prepared by contacting sorafenib dimethyl sulphoxide solvate of Formula III with water at room temperature, heating the reaction mixture to about 75° C. and stirring the reaction mixture for about 4 hours. In another preferred embodiment, sorafenib free base of Formula I may be prepared by contacting sorafenib dimethyl sulphoxide solvate of Formula III with water at room temperature and stirring the reaction mixture for about 17 hours.

In another embodiment, sorafenib free base of Formula I may be prepared by contacting sorafenib dimethyl sulphoxide solvate of Formula III with a chlorinated hydrocarbon solvent at a temperature of about −10° C. to about +10° C. and stirring the reaction mixture for about 5 minutes to about 1 hour. In a preferred embodiment, sorafenib free base of Formula I may be prepared by contacting sorafenib dimethyl sulphoxide solvate of Formula III with a chlorinated hydrocarbon solvent at a temperature of about 0° C. and stirring the reaction mixture for about 15 minutes to about 1 hour. The chlorinated hydrocarbon solvent may be selected from dichloromethane or chloroform, preferably dichloromethane.

In another embodiment, sorafenib free base of Formula I may be prepared by contacting sorafenib dimethyl sulphoxide solvate of Formula III with an alcohol at room temperature and stirring the reaction mixture for about 1 hour to about 8 hours, preferably for about 3 hours to about 4 hours. The alcohol may be selected from methanol, ethanol, iso-propanol or butanol.

In another embodiment, sorafenib free base of Formula I may be prepared by contacting sorafenib dimethyl sulphoxide solvate of Formula III with a ketone solvent at room temperature and stirring the reaction mixture for about 1 hour to about 8 hours, preferably for about 3 hours to about 4 hours. The ketone solvent may be selected from acetone, dimethyl ketone, ethyl methyl ketone or methyl iso-butyl ketone.

In another embodiment, sorafenib free base of Formula I may be prepared by contacting sorafenib dimethyl sulphoxide solvate of Formula III with an alkyl acetate solvent at room temperature and stirring the reaction mixture for about 1 hour to about 8 hours, preferably for about 3 hours to about 4 hours. The alkyl acetate may be selected from methyl acetate, ethyl acetate, propyl acetate or butyl acetate. Preferably, methyl acetate or ethyl acetate may be used.

In another embodiment, sorafenib free base of Formula I may be prepared by contacting sorafenib dimethyl sulphoxide solvate of Formula III with ether and stirring the reaction mixture at room temperature for about 30 minutes to about 8 hours, preferably for about 3 hours to about 4 hours. The ether may be selected from diethyl ether, ethyl methyl ether, tert-butyl methyl ether, tetrahydrofuran or 1,4-dioxane, preferably tert-butyl methyl ether.

Sorafenib free base of Formula I may also be obtained by heating sorafenib dimethyl sulphoxide solvate of Formula III to a temperature of above 110° C., in a vacuum oven. Heating may be carried out for about 1 hour to about 10 hours, preferably for about 4 hours.

In a particular embodiment, sorafenib free base of Formula I may be obtained by heating sorafenib dimethyl sulphoxide solvate of Formula III to a temperature of about 120° C. in a vacuum oven. In another embodiment, sorafenib free base of Formula I may be obtained by heating sorafenib dimethyl sulphoxide solvate of Formula III to a temperature of about 135° C. in a vacuum oven.

The processes of the present invention provide sorafenib free base of HPLC purity greater than 99%, preferably greater than 99.5%, more preferably about 99.9%.

Sorafenib acid addition salts of Formula IV may be prepared from sorafenib dimethyl sulphoxide solvate of Formula III by contacting sorafenib dimethyl sulphoxide solvate of Formula III with an acid of Formula HX. The acid of Formula HX may be selected from the group consisting of hydrochloric acid, hydrobromic acid, sulfuric acid, phosphoric acid, methanesulphonic acid, ethane sulphonic acid, trifluoromethanesulfonic acid, benzenesulfonic acid, p-toluene sulphonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid and mandelic acid.

The preparation of sorafenib acid addition salts of Formula IV may be carried out using solvent(s) selected from the group consisting of water, organic solvents containing at least one hydroxyl group, cyclic ethers, alkyl acetates, ketones, amides, nitriles, sulphoxides and mixtures thereof. Examples of organic solvents containing at least one hydroxyl group include methanol, ethanol, n-propanol, isopropanol, n-butanol, sec-butanol, isobutanol, n-pentanol, glycerol and ethylene glycol. Examples of cyclic ethers include tetrahydrofuran and 1,4-dioxane. Examples of alkyl acetates include methyl acetate, ethyl acetate, propyl acetate and butyl acetate. Examples of ketones include acetone, methyl ethyl ketone and methyl isobutyl ketone. Examples of amides include N,N-dimethylformamide and N,N-dimethylacetamide. Examples of nitriles include acetonitrile and propionitrile. Examples of sulphoxides include dimethyl sulfoxide and diethyl sulphoxide.

The acid of Formula HX may be added in a period of about 5 minutes to about 30 minutes. The reaction mixture may be stirred at a temperature of about 15° C. to the reflux temperature of the solvent for about 8 hours to about 16 hours.

In a particular embodiment, sorafenib tosylate of Formula II may be prepared by contacting sorafenib dimethyl sulphoxide solvate of Formula III with p-toluene sulphonic acid. Both anhydrous and hydrated forms of p-toluene sulphonic acid may be used. Preferably, p-toluene sulphonic acid monohydrate may be used.

p-Toluene sulphonic acid may be added to the reaction mixture containing sorafenib dimethyl sulphoxide solvate in a solvent as a solid or a solution of p-toluene sulphonic acid in water may be added.

In a particular embodiment, a solution of p-toluene sulphonic acid monohydrate in water may be added to the reaction mixture containing sorafenib dimethyl sulphoxide solvate in water or an organic solvent containing at least one hydroxyl group, such as methanol, ethanol, n-propanol, isopropanol, n-butanol, sec-butanol, isobutanol, n-pentanol, glycerol or ethylene glycol, preferably in water.

In another embodiment, sorafenib tosylate of Formula IV may be prepared by adding a solution of p-toluene sulphonic acid monohydrate in water to a suspension of sorafenib dimethyl sulphoxide solvate in water over a period of about 5 minutes to about 15 minutes and stirring the reaction mixture at about 60° C. to about 100° C., preferably at about 80° C., for about 8 hours to about 16 hours, preferably for about 12 hours.

In another embodiment, sorafenib tosylate of Formula IV may be prepared by adding a solution of p-toluene sulphonic acid in water to a suspension of sorafenib dimethyl sulphoxide solvate in water over a period of about 5 minutes to about 15 minutes and stirring the reaction mixture at room temperature for about 8 hours to about 16 hours, preferably for about 12 hours.

In the experiments involving preparation of sorafenib acid addition salts of Formula IV from sorafenib dimethyl sulphoxide solvate of Formula III, sorafenib free base may be optionally isolated from the reaction mixture.

The processes of the present invention provides sorafenib tosylate having HPLC purity greater than 99%, preferably greater than 99.5%, more preferably greater than 99.8%.

Polymorphs and pseudomorphs of sorafenib dimethyl sulphoxide solvate of Formula III are also included within the scope of the present invention.

Sorafenib dimethyl sulphoxide solvate of Formula III may be administered as part of a pharmaceutical composition for the treatment of cancer. Accordingly, in a further aspect, there is provided a pharmaceutical composition comprising sorafenib dimethyl sulphoxide solvate of Formula III and one or more pharmaceutically acceptable carriers, diluents or excipients and optionally other therapeutic ingredients. Pharmaceutical compositions comprising sorafenib dimethyl sulphoxide solvate of Formula III may be administered orally, topically, parenterally, by inhalation or spray, rectally or in the form of injectables. The injectable compositions may include intravenous, intramuscular, subcutaneous and parenteral injections, as well as, use of infusion techniques.

The HPLC method of the present invention is advantageous as it can be used for the identification and quantification of a wide range of related substances of sorafenib, for reaction monitoring and for determining chromatographic purity of sorafenib or pharmaceutically acceptable salts, polymorphs, pseudomorphs and solvates thereof. Additionally, the HPLC method of the present invention has the following advantages:
  Easy set-up.
  Less time-consuming.
  Results are reproducible.
  Involves use of an acidic buffer and does not involve use of any salts due to which HPLC column can be used for a longer time. Thus, the method is instrument-friendly.
  Does not require any pH adjustment.

In the foregoing section, embodiments are described by way of examples to illustrate the processes of invention. However, these are not intended in any way to limit the scope of the present invention. Several variants of the examples would be evident to persons ordinarily skilled in the art which are within the scope of the present invention.

Methods

The HPLC method of the present invention is described as follows:

A) Reagents, Solvents and Standards:
  Water (HPLC Grade)
  Orthophosphoric acid (88%, AR Grade)
  Methanol (HPLC Grade)

B) Chromatographic Conditions:
  Column: Zorbax SB AQ, 250 mm×4.6 mm, 5 μm
  Flow rate: 1.0 mL/minute
  Detector: UV at 260 nm
  Injection volume: 10 μL
  Column oven Temperature: 30° C.
  Run time: 50 minutes
  Buffer: Orthophosphoric acid in water
  Mobile Phase: Buffer and Methanol
  Diluent: Pre-mixed and degassed solution of buffer and methanol (40:60; v/v)
  Gradient

| Time | Methanol | Buffer |
| --- | --- | --- |
| 0 | 10 | 90 |
| 5 | 10 | 90 |
| 35 | 85 | 15 |
| 40 | 85 | 15 |
| 43 | 10 | 90 |
| 50 | 10 | 90 |

C) Preparation of Buffer 1 mL of orthrophosphoric acid was transferred into a volumetric flask. Water (1000 mL) was added. The contents were mixed thoroughly and filtered through 0.45 micron or finer porosity membrane filter.

D) Preparation of Diluent

A pre-mixed and degassed solution of buffer and methanol in the ratio of 40:60 (v/v) was used as a diluent.

E) Preparation of Standard Solution 25 mg of accurately weighed sorafenib tosylate working standard was transferred into a 200 mL volumetric flask. Methanol (3 mL) was added and the contents were sonicated till complete dissolution takes place. 5 mL of this solution was diluted to 50 mL by adding diluent. 5 mL of the resultant solution was further diluted to 25 mL by adding diluent. The final solution was filtered through 0.45 micron nylon filter.

F) Preparation of Sample Solution 25 mg of accurately weighed sorafenib tosylate was transferred to a 200 mL volumetric flask. Methanol (3 mL) was added and the contents were sonicated till complete dissolution takes place. The volume was made up by adding diluent. The resultant solution was filtered through 0.45 micron nylon filter.

G) Preparation of Blank

Methanol (3 mL) was transferred to a 50 mL volumetric flask and the volume was made up by adding diluent.

H) Evaluation of System Suitability

The standard solution was injected into the chromatograph for recording the chromatogram. The system was considered to be suitable for analysis only if the following conditions were met:
  USP tailing factor of peak corresponding to sorafenib was not more than 1.5.
  Percentage RSD of five replicate injections of standard solutions was not more than 2%.

I) Procedure

After system suitability evaluation, chromatograms were recorded by separately injecting blank and sample solution into the chromatograph. The blank chromatogram was examined for any extraneous peaks to disregard the corresponding peaks observed in the chromatogram of the sample solution.

The retention times (RT) and relative retention times (RRT), in minutes, for the compounds resolved using the HPLC method of the present invention is provided below:

| Compound | RT | RRT |
|---|---|---|
| 4-(2-(N-methylcarbamoyl)-4-(pyridyloxy) aniline | 18.32 | 0.50 |
| 4-chloro-N-methyl-2-pyridinecarboxamide | 23.21 | 0.64 |
| 4-chloro-3-(trifluoromethyl) phenyl isocyanate | 32.00 | 0.88 |
| Sorafenib | 36.38 | 1.0 |

X-ray diffraction patterns were recorded using Panalytical Expert PRO with Xcelerator as detector, 3-40 as scan range, 0.02 as step size and 3-40° 2θ as range.

DSC and TGA were recorded using Mettler Toledo DSC 821e and TA instrument-Q 500, respectively.

Moisture content was measured by Karl-Fischer method

EXAMPLES

Non-limiting examples of the present invention are as follows.

Example 1

Preparation of Sorafenib Free Base

A solution of 4-chloro-3-(trifluoromethyl)phenyl isocyanate (101.1 g) in dichloromethane (250 mL) was added to a reaction mixture containing 4-(2-(N-methylcarbamoyl)-4-pyridyloxy)aniline (110.0 g) in dichloromethane (250 mL) at about 0° C. in about 30 minutes. The reaction mixture was stirred at room temperature for about 16 hours. The resulting solid was filtered, washed with dichloromethane (2×200 mL) and dried under reduced pressure at about 35° C. for about 4 hours to obtain sorafenib free base.

Yield: 52.3%; HPLC Purity: 97.86%

Example 2

Preparation of Sorafenib Dimethyl Sulphoxide Solvate

Method A:

A reaction mixture containing sorafenib free base (10 g) in dimethyl sulphoxide (15 mL) was stirred at about 45° C. for about 10 minutes. The solution was slowly cooled to about 25° C. in about 15 minutes. The solution was stirred for about 2 hours. The resulting solid was filtered, washed with water (3×20 mL) and dried under reduced pressure at about 50° C. for about 5 hours to obtain sorafenib dimethyl sulphoxide solvate.

Yield: 68%; HPLC purity: 99.43%

Method-B:

A reaction mixture containing sorafenib free base (40 g) in dimethyl sulphoxide (15 mL) was stirred at about 60° C. for about 20 minutes. The solution was slowly cooled to about 25° C. in about 20 minutes. The solution was stirred for about 8 hours. The resulting solid was filtered and dried under reduced pressure at about 50° C. for about 12 hours to obtain sorafenib dimethyl sulphoxide solvate.

Yield: 81.3%; HPLC purity: 99.75%

Method C:

A reaction mixture containing sorafenib free base (12 g) in dimethyl sulphoxide (18 mL) was stirred at room temperature for about 5 hours. The resulting solid was filtered, washed with water (2×20 mL) and dried at about 45° C. for about 12 hours in an air oven to obtain sorafenib dimethyl sulphoxide solvate.

Yield: 74.9%

Example 3

Preparation of Sorafenib Free Base by Desolvation of Sorafenib Dimethyl Sulphoxide Solvate in Different Solvents Method A:

Water (10 mL) was added to sorafenib dimethyl sulphoxide solvate (1 g) at room temperature. The reaction mixture was stirred at about 75° C. for about 4 hours. The resulting solid was filtered and dried under reduced pressure at about 45° C. for about 4 hours to obtain sorafenib free base.

Yield: 75.9%

Method B:

Water (10 mL) was added to sorafenib dimethyl sulphoxide solvate (1 g) at room temperature. The reaction mixture was stirred for about 17 hours. The resulting solid was filtered and dried under reduced pressure at about 40° C. for about 4 hours to obtain sorafenib free base.

Yield: 84.1%

Method C:

Dichloromethane (10 mL) was added to sorafenib dimethyl sulphoxide solvate (1 g) at a temperature of about 0° C. The reaction mixture was stirred for about 15 minutes to obtain a solution. The solution was stirred for about 10 minutes. The resulting solid was filtered and dried under reduced pressure at about 40° C. for about 1 hour to obtain sorafenib free base.

Yield: 93.5%; HPLC purity: 99.78%

Method D:

Methanol (10 mL) was added to sorafenib dimethyl sulphoxide solvate (1 g) at room temperature. The reaction mixture was stirred. The resulting solid started appearing after about 5 minutes. The reaction mixture was stirred for about 4 hours, filtered and dried under reduced pressure at about 45° C. for about 5 hours to obtain sorafenib free base.

Yield: 87.6%; HPLC Purity: 99.79%

Method E:

Ethanol (10 mL) was added to sorafenib dimethyl sulphoxide solvate (1 g) at room temperature. The reaction mixture was stirred. A solid started appearing after about 5 minutes. The reaction mixture was stirred for about 4 hours, filtered and dried under reduced pressure at about 45° C. for about 5 hours to obtain sorafenib free base.

Yield: 76.4%; HPLC Purity: 99.81%

Method F:

Iso-propanol (10 mL) was added to sorafenib dimethyl sulphoxide solvate (1 g) at room temperature. The reaction mixture was stirred for about 4 hours. The reaction mixture was filtered and dried under reduced pressure at about 45° C. for about 4 hours to obtain sorafenib free base.

Yield: 52.5%; HPLC Purity: 99.82%

Method G:

Acetone (10 mL) was added to sorafenib dimethyl sulphoxide solvate (1 g) at room temperature. The reaction mixture was stirred. A solid started appearing after about 5 minutes. The reaction mixture was stirred for about 4 hours, filtered and dried under reduced pressure at about 40° C. for about 4 hours to obtain sorafenib free base.

Yield: 58.4%

Method H:

Methyl acetate (15 mL) was added to sorafenib dimethyl sulphoxide solvate (1.5 g) at room temperature. The suspension was stirred for about 4 hours, filtered and dried under reduced pressure at about 45° C. for about 4 hours to obtain sorafenib free base.

Yield: 28.9%; HPLC Purity: 99.73%

Method I:

Ethyl acetate (10 mL) was added to sorafenib dimethyl sulphoxide solvate (1.5 g) at room temperature. The suspension was stirred for about 4 hours, filtered and dried under reduced pressure at about 45° C. for about 4 hours to obtain sorafenib free base.

Yield: 34.4%; HPLC Purity: 99.9%

Method J:

Methyl ethyl ketone (15 mL) was added to sorafenib dimethyl sulphoxide solvate (1.5 g) at room temperature. The reaction mixture was stirred. A solid started appearing after about 5 minutes. The reaction mixture was stirred for about 4 hours, filtered and dried under reduced pressure at about 45° C. for about 4 hours to obtain sorafenib free base.

Yield: 51.4%; HPLC Purity: 99.74%

Method K:

Methyl iso-butyl ketone (15 mL) was added to sorafenib dimethyl sulphoxide solvate (1.5 g) at room temperature. The reaction mixture was stirred. A solid started appearing after about 5 minutes. The reaction mixture was stirred for about 4 hours, filtered and dried under reduced pressure at about 45° C. for about 4 hours to obtain sorafenib free base.

Yield: 57.4%; HPLC Purity: 99.88%

Example 4

Preparation of Sorafenib Free Base by Heating Sorafenib Dimethyl Sulphoxide Solvate Sorafenib dimethyl sulphoxide solvate (7 g) was divided into seven equal portions and each portion was kept at a different temperature for about 4 hours in a vacuum oven. No change was observed on heating for about 4 hours in the temperature range of about 45° C. up to 110° C. in a vacuum oven. Desolvation of sorafenib dimethyl sulphoxide solvate to sorafenib free base was observed on heating to a temperature of about 120° C. and about 135° C. for about 4 hours in a vacuum oven.

Example 5

Preparation of Sorafenib Tosylate

Method A:

Water (10 mL) was added to sorafenib dimethyl suphoxide solvate (2 g). The reaction mixture was stirred for about 5 minutes. A solution of p-toluene sulphonic acid monohydrate (1.41 g) in water (10 mL) was added in a period of about 10 minutes to the above reaction mixture. The resulting reaction mixture was stirred for about 12 hours at about 80° C. to obtain a solid, washed with water (2×10 mL) and dried under reduced pressure at about 50° C. for about 5 hours to obtain sorafenib tosylate.

Yield: 89.3%; HPLC Purity: 99.81%

Method B:

Water (5 mL) was added to sorafenib dimethyl suphoxide solvate (1 g). The reaction mixture was stirred for about 5 minutes. A solution of p-toluene sulphonic acid monohydrate (1.41 g) in water (5 mL) was added in a period of about 10 minutes to the above reaction mixture. The resulting reaction mixture was stirred for about 12 hours at room temperature to obtain a solid, washed with water (2×10 mL) and dried under reduced pressure at about 45° C. for about 5 hours to obtain sorafenib tosylate.

Yield: 82%; HPLC Purity: 99.71%

We claim:

1. Sorafenib dimethyl sulphoxide solvate of Formula III

FORMULA III characterized by X-ray diffraction peaks at d-spacing 5.20, 4.21, 4.16, 3.83 and 3.66 Å.

2. Sorafenib dimethyl sulphoxide solvate according to claim 1 further characterized by X-ray diffraction peaks at d-spacing 5.36, 4.47, 4.44, 3.26 and 3.14 Å.

Figure 1:
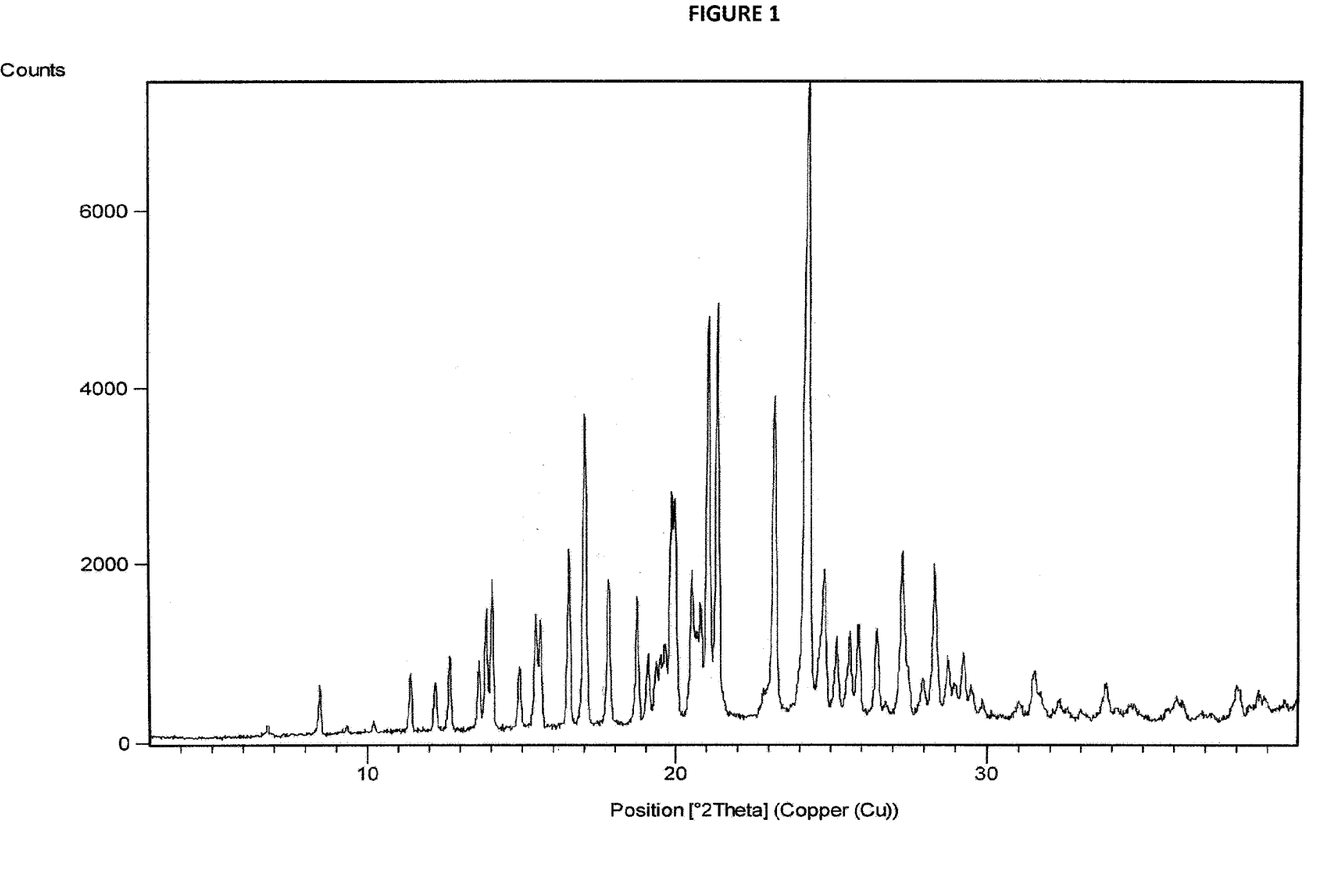
FIG. 1: X-ray Diffraction (XRD) pattern of sorafenib dimethyl sulphoxide solvate

3. Sorafenib dimethyl sulphoxide solvate of Formula III characterized by X-ray diffraction pattern as depicted in FIG. 1.

4. Sorafenib dimethyl sulphoxide solvate of Formula III characterized by DSC thermogram having endotherms at about 123.69° C. and about 202.54° C.

Figure 2:
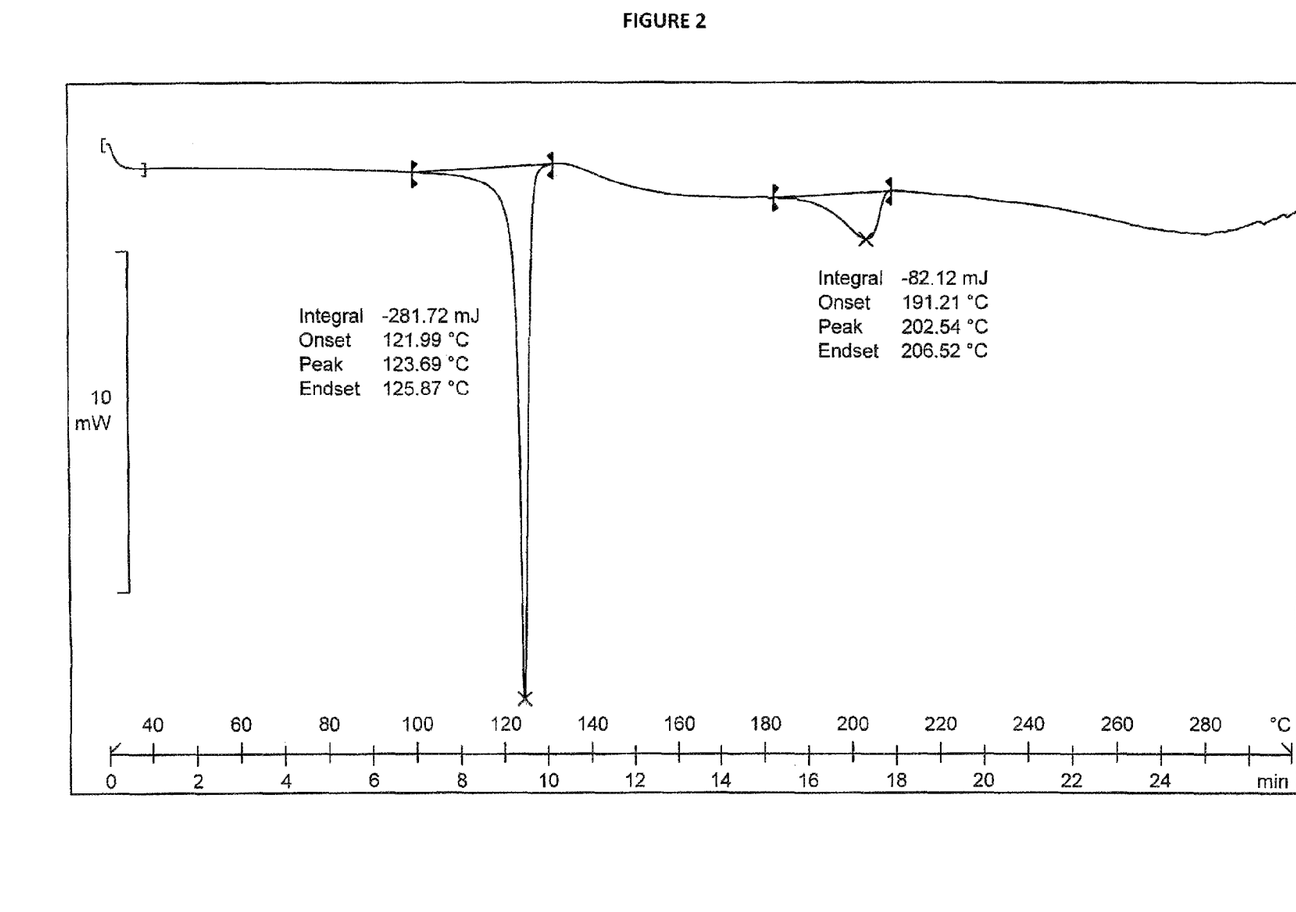
FIG. 2: Differential Scanning calorimetry (DSC) thermogram of sorafenib dimethyl sulphoxide solvate

5. Sorafenib dimethyl sulphoxide solvate of Formula III characterized by DSC thermogram as depicted in FIG. 2.

6. Sorafenib dimethyl sulphoxide solvate of Formula III characterized by X-ray diffraction pattern as depicted in FIG. 1 and DSC thermogram as depicted in FIG. 2.

Figure 3:
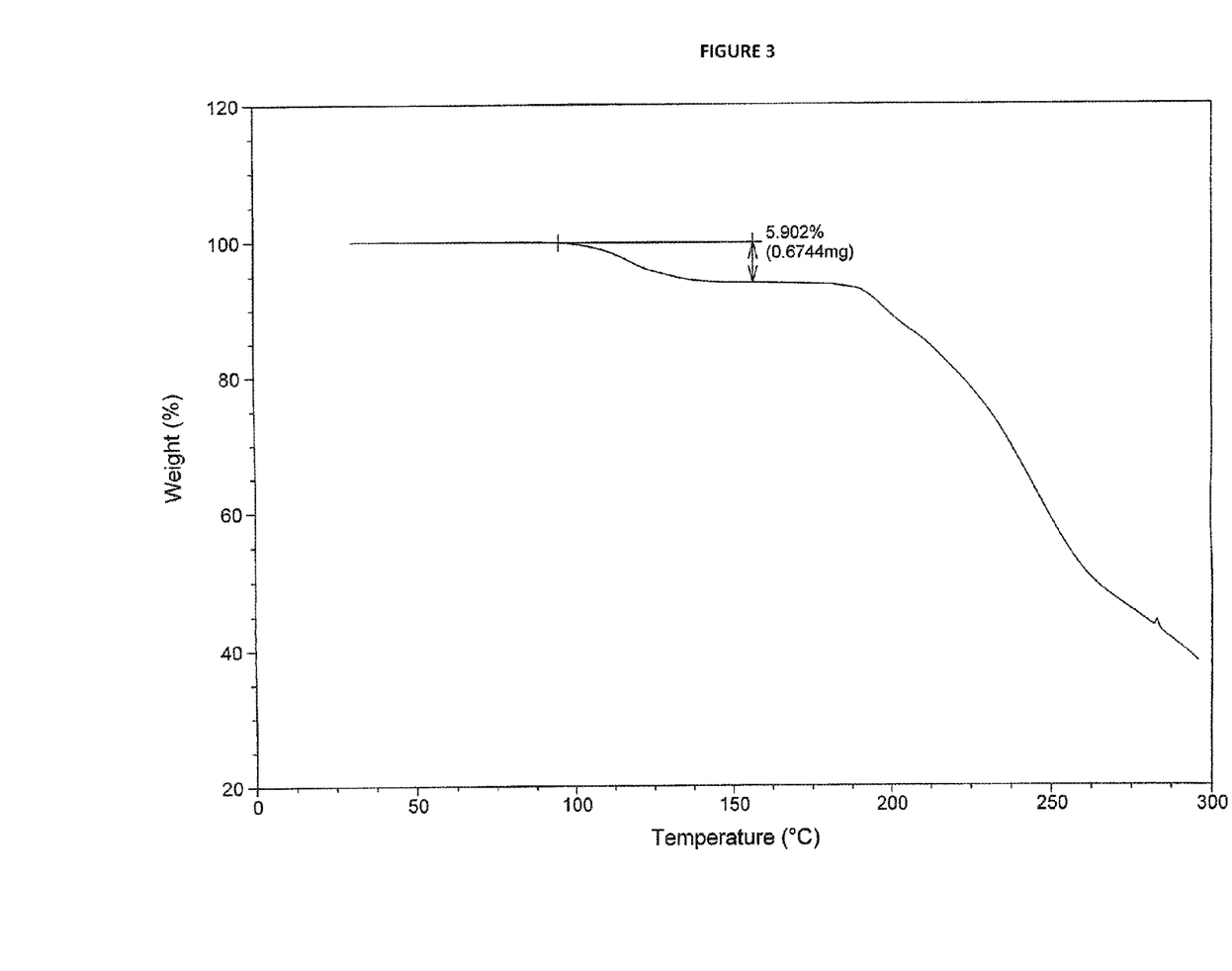
FIG. 3: Thermogravimetric Analysis (TGA) curve of sorafenib dimethyl sulphoxide solvate

7. Sorafenib dimethyl sulphoxide solvate of Formula III characterized by TGA as depicted in FIG. 3.

Figure 4:
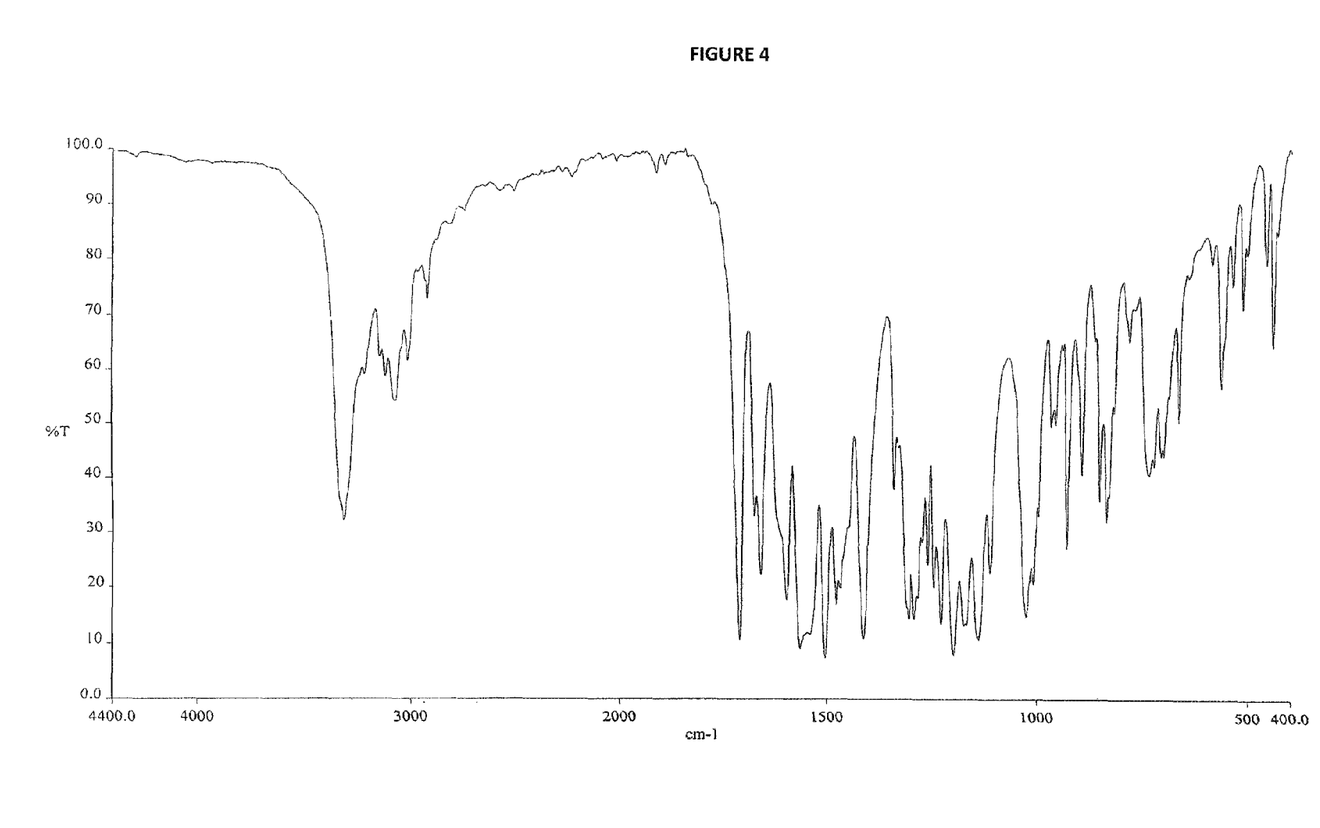
FIG. 4: Infra-red (IR) spectrum of sorafenib dimethyl sulphoxide solvate
Figure 5:
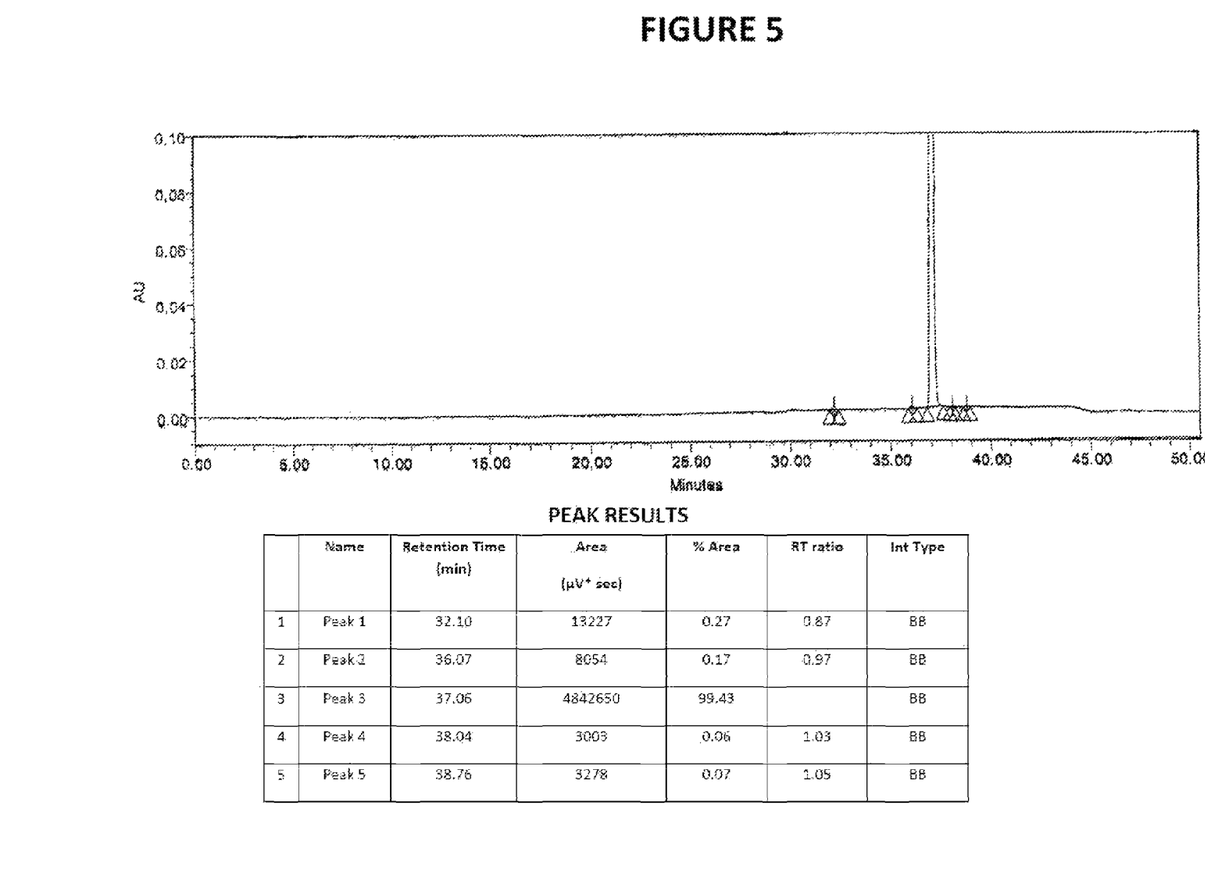
FIG. 5: HPLC chromatogram of sorafenib dimethyl sulphoxide solvate
Figure 6:
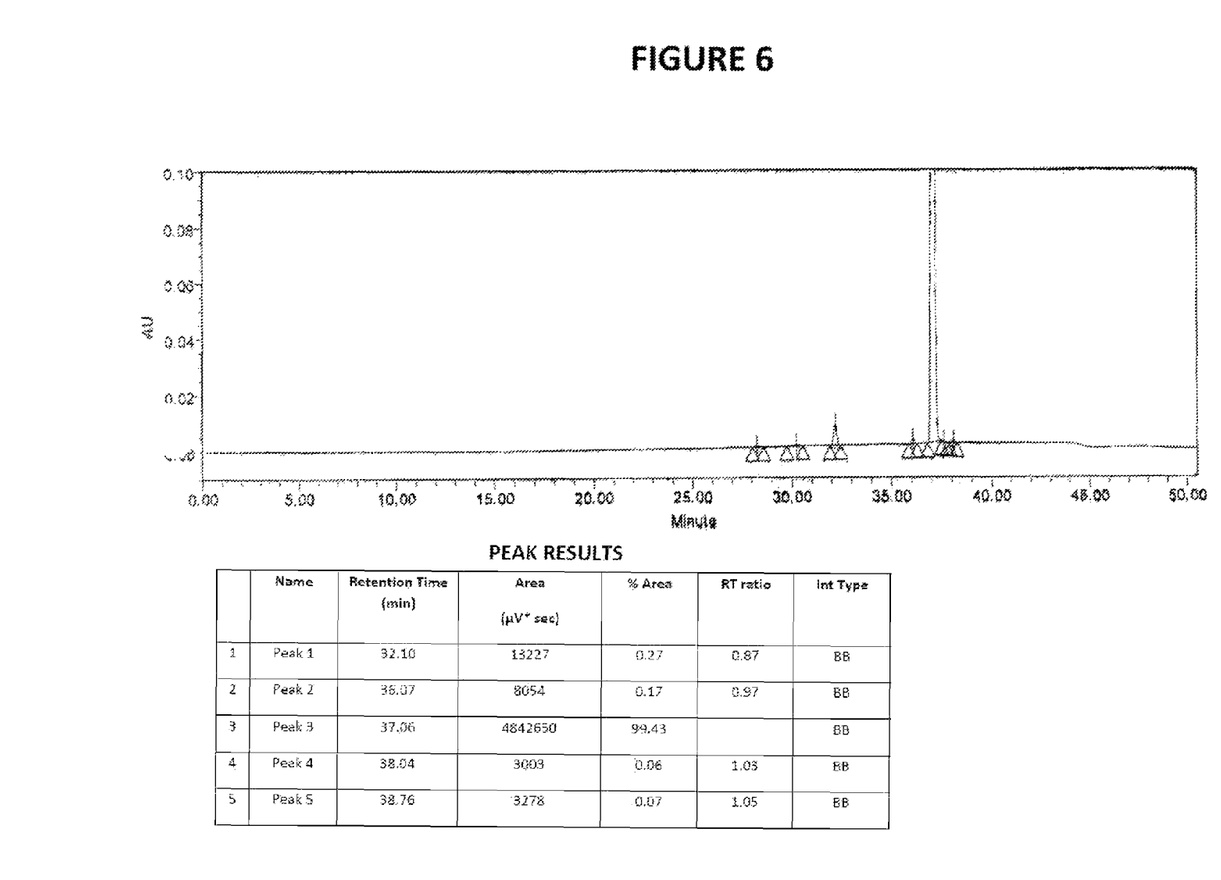
FIG. 6: HPLC chromatogram of sorafenib free base to be used for the preparation of sorafenib dimethyl sulphoxide solvate
Figure 7:
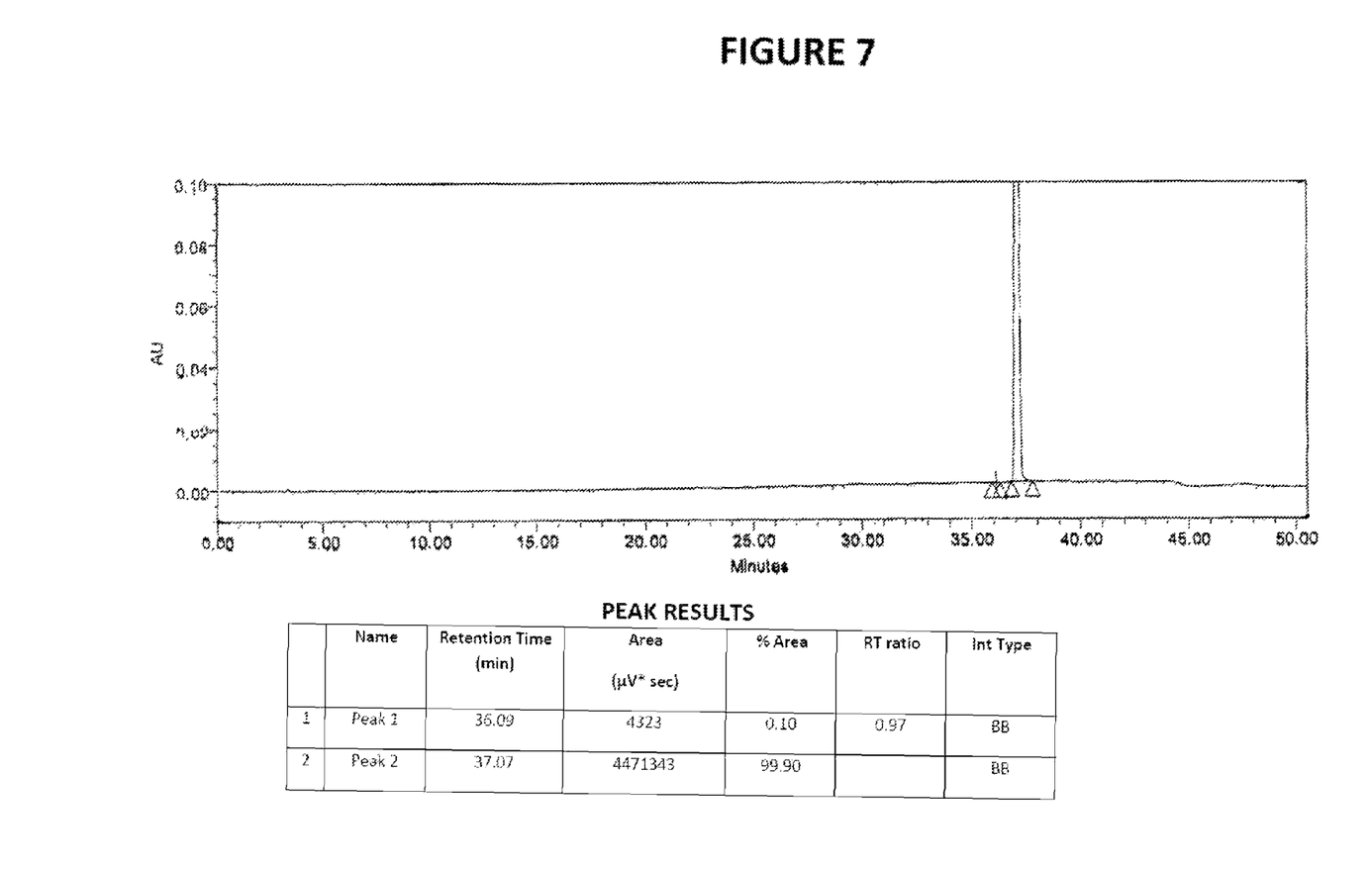
FIG. 7: HPLC chromatogram of sorafenib free base obtained by desolvation of sorafenib dimethyl sulphoxide solvate
Figure 8:
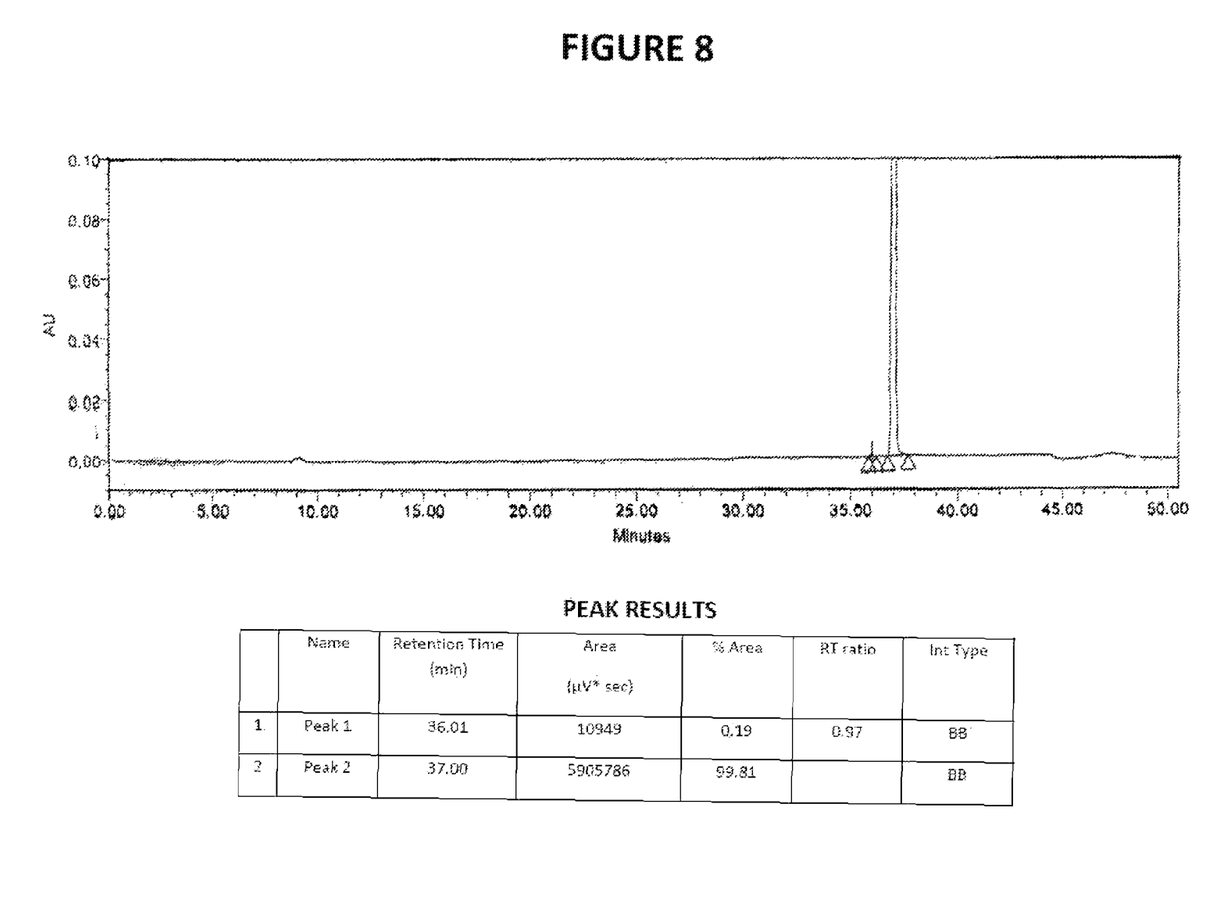
FIG. 8: HPLC chromatogram of sorafenib tosylate
Figure 9:
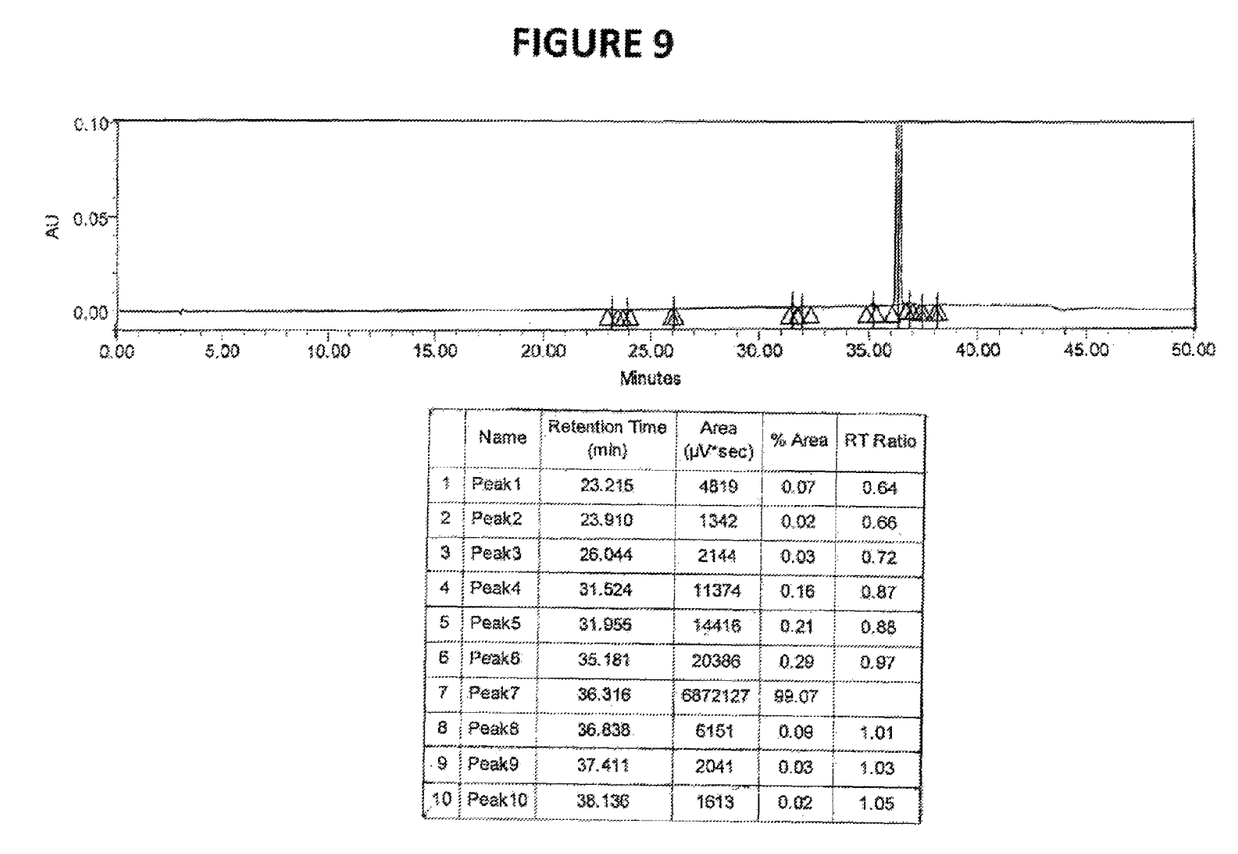
FIG. 9: HPLC chromatogram of sorafenib free base
Figure 10:
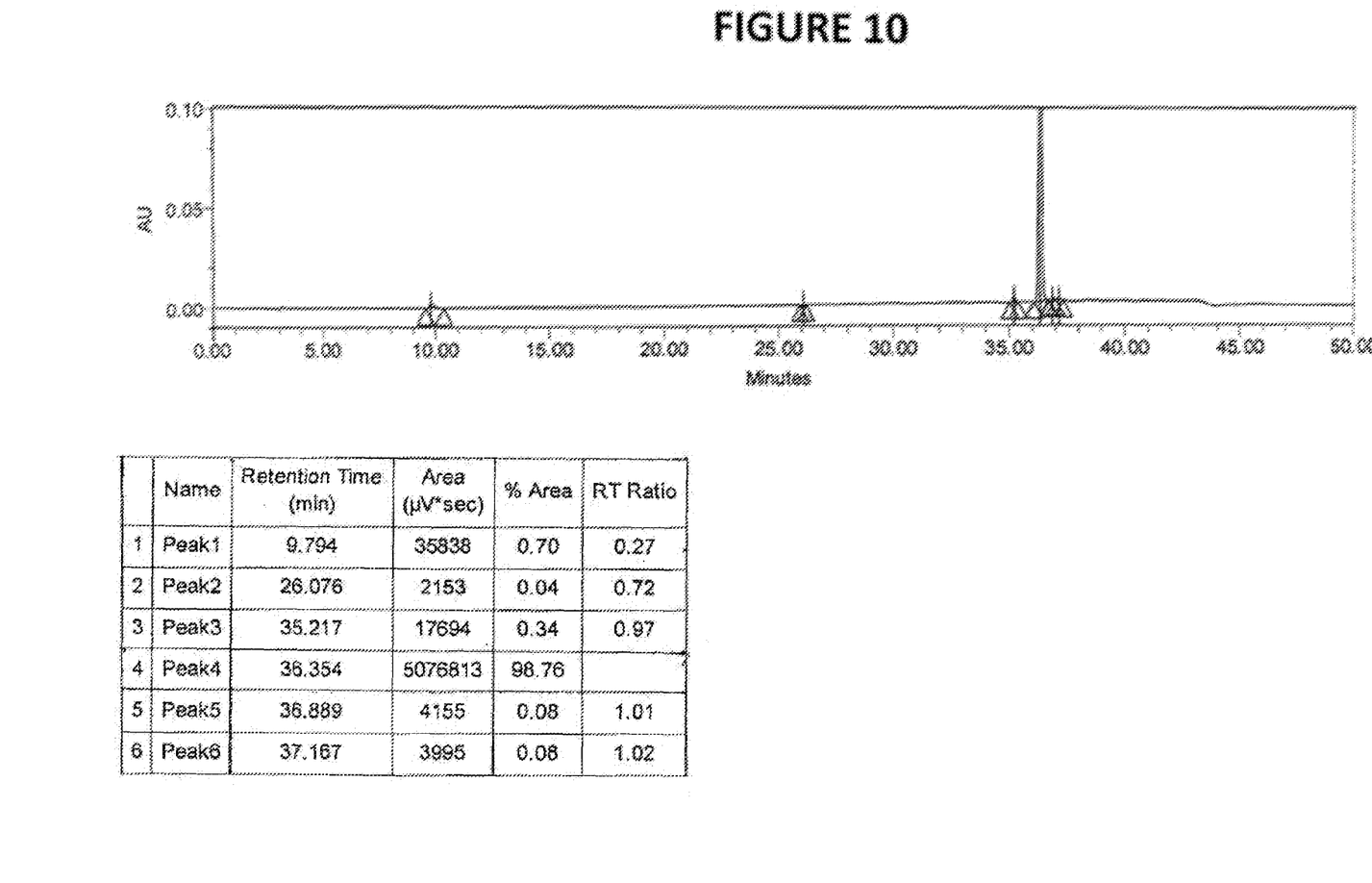
FIG. 10: HPLC chromatogram of sorafenib tosylate

8. Sorafenib dimethyl sulphoxide solvate of Formula III characterized by IR spectrum as depicted in FIG. 4.

9. Sorafenib dimethyl sulphoxide solvate of Formula III having purity greater than 99% by HPLC.

10. A process for the preparation of sorafenib dimethyl sulphoxide solvate of Formula III

FORMULA III comprising contacting sorafenib free base of Formula I

FORMULA I with dimethyl sulphoxide.

11. The process according to claim 10, wherein Sorafenib free base of Formula I is contacted with dimethyl sulphoxide at a temperature of about 15° C. to the reflux temperature of dimethyl sulphoxide.

12. A pharmaceutical composition comprising the sorafenib dimethyl sulphoxide solvate of Formula III according to claim 1 and one or more pharmaceutically acceptable carriers, diluents or excipients.

* * * * *